(12) United States Patent
Geppert et al.

(10) Patent No.: US 6,958,433 B2
(45) Date of Patent: Oct. 25, 2005

(54) TRANSGENIC MICE OVEREXPRESSING ASPARTYL PROTEASE 2 (ASP2)

(75) Inventors: Martin Geppert, Ilford (GB); Alexander James Harper, Harlow (GB); Steve Mark Harrison, Harlow (GB); Haydn Prosser, Ware (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/223,837

(22) Filed: Aug. 20, 2002

(65) Prior Publication Data

US 2004/0154049 A1 Aug. 5, 2004

(30) Foreign Application Priority Data

Aug. 21, 2001 (GB) .............................................. 0120342
Nov. 11, 2001 (GB) .............................................. 0126732

(51) Int. Cl.[7] ...................... A01K 67/027; C07H 21/04; C12N 5/10; C12N 5/18
(52) U.S. Cl. .......................... 800/18; 800/12; 536/23.1; 536/23.5; 536/24.1; 435/354
(58) Field of Search .............................. 800/13, 12, 18; 536/23.1, 23.5, 24.1; 435/354

(56) References Cited

U.S. PATENT DOCUMENTS 6,509,190 B2 * 1/2003 Kandel et al. ............... 435/354
6,699,671 B1 * 3/2004 Gurney et al. ................ 435/7.1

OTHER PUBLICATIONS

Harrison et al. BACE1 (beta–secretase) transgenic and knockout mice: identification of neurochemical deficits and behavioral changes. Mol Cell Neurosci. vol. 24, No. 3, pp. 646–655, Nov. 2003.*
Sigmund et al. Viewpoint: Are studies in genetically altered mice out of control? Anterioscler. Thromb. Vasc. Biol., vol. 20, No. 6, pp. 1425–1429, 2000.*
Wall. Transgenic livestock: progress and prospects for the future. Theriogenology. vol. 45, No. 1, pp. 57–68, 1996.*
Acquati et al., "The gene encoding DRAP (BACE2), a glycosylated transmembrane protein of the aspartic protease family, maps to the Down critical region," *FEBS Letters* 468:59–64 (2000).
Dyrks et al., "Identification, transmembrane orientation and biogenesis of the amyloid A4 precursor of Alzheimer's disease," *The EMBO Journal* 7(4):949–957 (1988).
Dyrks et al, "Generation of βA4 from the anyloid protein precursor and fragments thereof," *FEBS Letters* 335(1):89–93 (Nov. 1993).
Haass et al., "β–Amyloid peptide and a 3–kDa fragment are derived by distinct cellular mechanisms," *The Journal of Biological Chemistry* 268(5):3021–3024 (Feb. 1993).

Hussain et al., "Identification of a novel aspartic protease (Asp 2) as β–Secretase," *Molecular and Cellular Neuroscience* 14(6):419–427 (1999).
Hussain et al., "ASP1 (BACE2) cleaves the amyloid precursor protein at the β–Secretase site," *Molecular and Cellular Neuroscience* 16:609–619 (2000).
Janus et al., "Transgenic mouse models of Alzheimer's disease," *Biochimica et Biophysica Acta* 1502(1):63–75 (Jul. 2000).
Mayford et al., "Control of memory formation through regulated expression of a CaMKII transgene," *Science* 274:1678–1683 (Dec. 1996).
Moechars et al., "Early phenotypic changes in transgenic mice that overexpress different mutants of amyloid precursor protein in brain," *The Journal of Biological Chemistry* 274(10):6483–6492 (Mar. 1999).
Rogers et al., "Behavioral and functional analysis of mouse phenotype: SHIRPA, a proposed protocol for comprehensive phenotype assessment," *Mammalian Genome* 8:711–713 (1997).
Suzuki et al., "An increased percentage of long amyloid βprotein secreted by familial amyloid βprotein precursor ($βAPP_{717}$) mutants," *Science* 264:1336–1340 (May 1994).
Tang et al., "Genetic enhancement of learning and memory in mice," *Nature* 401(6748):63–69 Sep. 1999).
Yan et al., "BACE2 functions as an alternative α–Secretase in cells," *The Journal of Biological Chemistry* 276(36):34019–34027 (Sep. 2001).
Harper et al., "Mouse models for AD; characterization of beta–secretase (Asp2) overexpressing mice using a novel gene expression strategy," *Society for Neuroscience Abstracts* 27(1):852 (Nov. 2001).
Hernandez–Sanchez et al., "Mice transgenically overexpressing sulfonylurea receptor 1 in forebrain resist seizure induction and excitotoxic neuron death," *Proc. Natl. Acad. Sci. USA* 98(6):3549–3554 (Mar. 2001).
Skovronsky et al., "beta–Secretase revealed: starting gate for race to novel therapies for Alzheimer's disease," *Trends in Pharmacological Sciences* 21(5):161–163 (May 2000).

* cited by examiner

*Primary Examiner*—Terry McKelvey
*Assistant Examiner*—Jennifer Dunston
(74) *Attorney, Agent, or Firm*—Virginia G. Campen

(57) ABSTRACT

The present invention provides a recombinant DNA construct comprising a coding sequence encoding human ASP2 and a brain-specific calcium calmodulin kinase promoter sequence which is operably linked to the coding sequence. The present invention further provides a transgenic non-human animal whose genome incorporates a polynucleotide comprising a coding sequence which encodes the human ASP2 protein wherein the coding sequence is operably linked to a brain-specific calcium calmodulin kinase II promoter.

3 Claims, 2 Drawing Sheets

Figure 1:
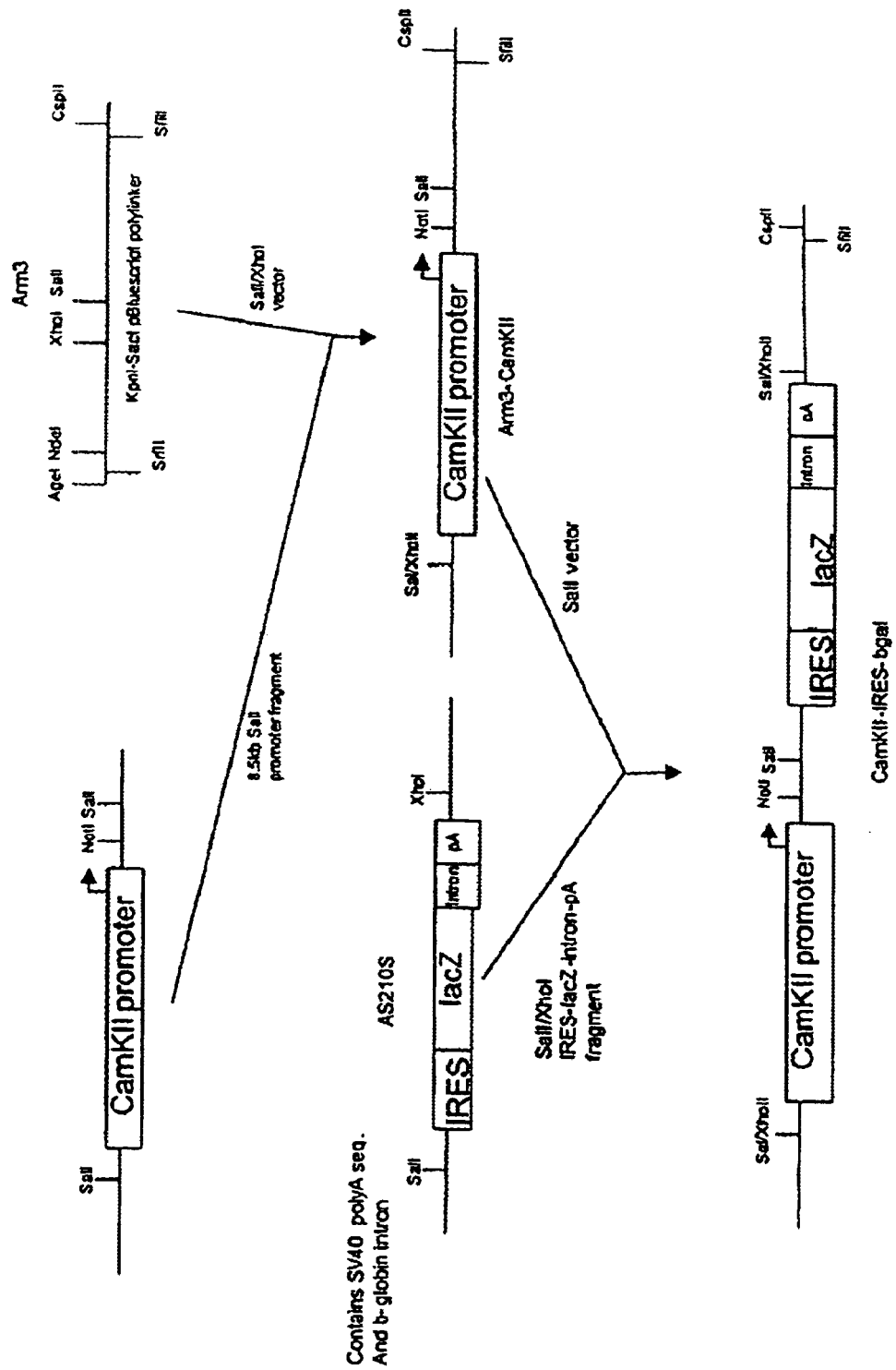

FIG. 1  Construction of CamKII-IRES-bgal vector

SEQUENCE LISTING

<160> NUMBER OF SEQ ID NOS: 1

<210> SEQ ID NO 1
<211> LENGTH: 501
<212> TYPE: PRT
<213> ORGANISM: homo sapien

<400> SEQUENCE: 1

```
Met Ala Gln Ala Leu Pro Trp Leu Leu Leu Trp Met Gly Ala Gly Val
 1               5                  10                  15

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp
        35                  40                  45

Glu Glu Pro Glu Glu Pro Gly Arg Arg Gly Ser Phe Val Glu Met Val
    50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu Met Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Val Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Val Pro
        195                 200                 205

Asn Leu Phe Ser Leu Gln Leu Cys Gly Ala Gly Phe Pro Leu Asn Gln
    210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
        275                 280                 285

Asp Ser Gly Thr Thr Asn Leu Arg Leu Pro Lys Lys Val Phe Glu Ala
    290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
```

-continued

```
             355                 360                 365
Pro Val Glu Asp Val Ala Thr Ser Gln Asp Asp Cys Tyr Lys Phe Ala
        370                 375                 380

Ile Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala Cys His Val His Asp Glu Phe Arg Thr Ala Ala Val Glu
                420                 425                 430

Gly Pro Phe Val Thr Leu Asp Met Glu Asp Cys Gly Tyr Asn Ile Pro
            435                 440                 445

Gln Thr Asp Glu Ser Thr Leu Met Thr Ile Ala Tyr Val Met Ala Ala
        450                 455                 460

Ile Cys Ala Leu Phe Met Leu Pro Leu Cys Leu Met Val Cys Gln Trp
465                 470                 475                 480

Arg Cys Leu Arg Cys Leu Arg Gln Gln His Asp Asp Phe Ala Asp Asp
                485                 490                 495

Ile Ser Leu Leu Lys
            500
```

TRANSGENIC MICE OVEREXPRESSING ASPARTYL PROTEASE 2 (ASP2)

This invention relates to transgenic animals and their use as models of Alzheimer's disease.

RELATED APPLICATIONS

This application claims priority from Great Britain Application No. 0120342.1 filed in the United Kingdom on Aug. 21, 2001, and Great Britain Application No. 0126723.6 filed in the United Kingdom on Nov. 11, 2001.

BACKGROUND TO THE INVENTION

The main protein component of the amyloid plaques found in the brain of Alzheimer's disease (AD) patients is Aβ, a 4 kDa peptide consisting of mainly forty and forty-two residues ($A\beta_{1-40}$, $A\beta_{1-42}$) being derived from the amyloid precursor protein (APP). APP can be cleaved at the N-terminus of Aβ by an enzyme called β-secretase generating a soluble APP and the C-terminal fragment A4CT (C99). This 99 residue long membrane protein A4CT (ref. 1) which is the direct precursor for Aβ contains the entire Aβ domain, the membrane domain and the cytoplasmic tail of APP. β-secretase is thought to be a protein called aspartyl protease 2 (Asp 2). Contradictory evidence exists as to whether a highly homologous protein, aspartyl protease 1 (Asp 1) also has β-secretase activity (Refs 2, 3). It is thought that Asp 1 may play a role in amyloidogenesis in peripheral rather than brain tissues.

Both C-terminal fragments of APP, A4CT and p3CT, are cleaved within the membrane domain by a γ-cleavage activity, thereby releasing Aβ and p3 into the medium (refs. 4, 5). In cells expressing wild type APP the site of γ-cleavage is mainly the peptide bond Val(40)-Ile(41) of A4CT and to a minor extent the bond Ala(42)-Thr(43). In cells expressing APP with the Familial AD linked mutations at Val 717 (based on $APP_{770}$, Val 46 of A4CT) an increased γ-cleavage occurs behind Val(42), thus producing larger amounts of $A\beta_{1-42}$ (ref. 6).

Several groups have attempted to develop transgenic mouse models that demonstrate convincing pathology indicative of alzheimers disease (AD) such as the PDAPP mice, Tg2576, TgAPP/Sw/1, etc (Reviewed in ref 7) However, no transgenic mouse models have yet been produced which overexpress human β-secretase (Asp 2). This enzyme is one of the two key enzymes that cleave Amyloid Precursor Protein to liberate the β-amyloid peptide, the major constituent of amyloid plaques in Alzhemier Disease brain. It is likely that such mice will develop convincing pathology as over-expression of this enzyme will increase the level of cleavage of Amyloid Precursor Protein at the β-site. Therefore this would represent a novel model of AD as all existing transgenic animal models rely upon the expression of mutant forms of human genes which are linked to early onset Alzheimer's Disease (Amyloid Precursor Protein and Presenilin-1). Such a model should represent a faithful model system for the production and deposition of amyloid deposits characterisitic of Alzheimer's disease.

Results obtained depend upon the source of the promoter and the protein coding sequence used. We have found that the use of a specific neuronal promoter will increase the possibility of the development of pathology that resembles the clinical situation.

A BRIEF DESCRIPTION OF THE FIGURES

Figure 2:
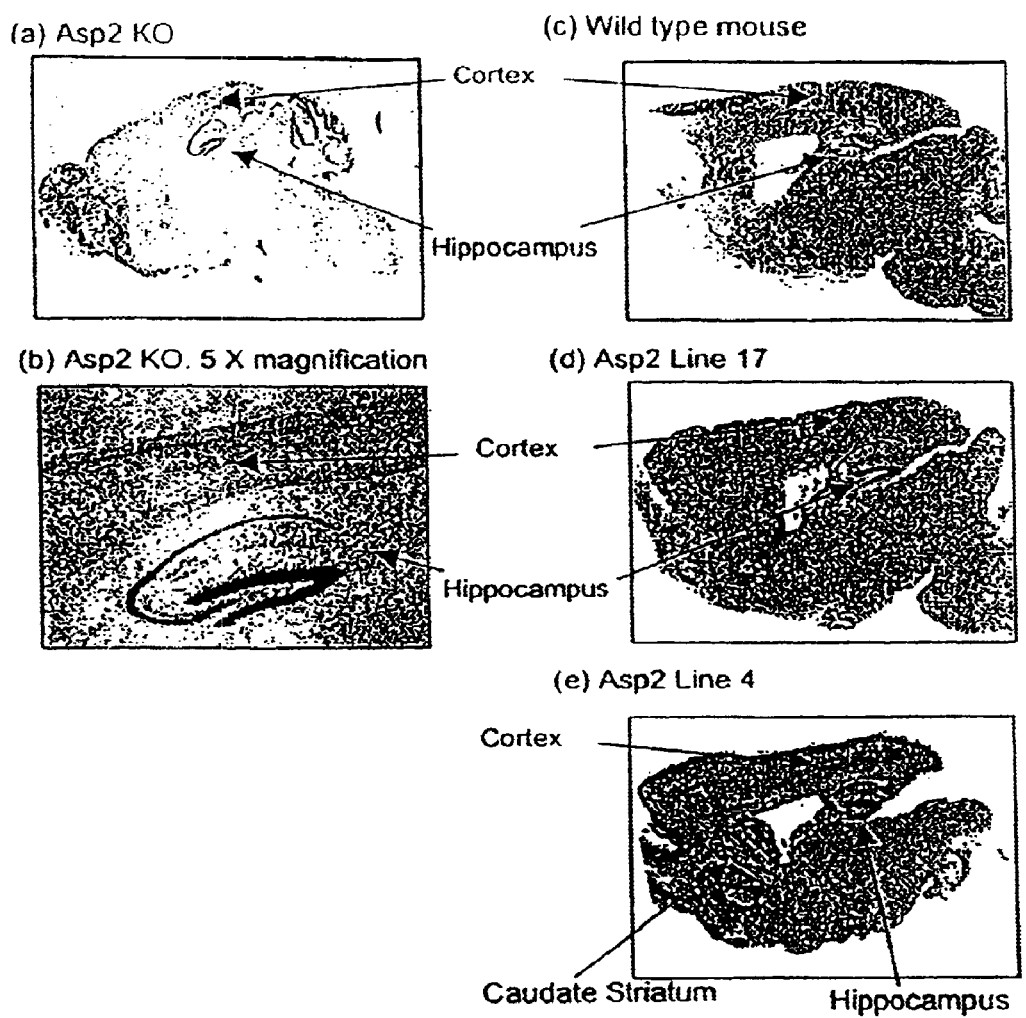

FIG. 1—this describes in pictorial form the cloning strategy used to form the vector IRES β-gal FIG. 2—the results show expression of LacZ and hence the transgene in knockout mice where LacZ was expressed under the control of the endogenous Asp2 promoter (a and b) and in the overexpressor transgenic mice of the invention (d and e). The figure also demonstrates that no LacZ expression was seen in Wild Type mice (c).

DETAILED DESCRIPTION OF THE INVENTION

The present invention accordingly provides a non-human transgenic animal whose genome incorporates a nucleotide sequence encoding the human ASP2 protein, which nucleotide sequence is operatively linked to mouse CaM-kinase-II promoter. By the term "ASP2 protein" is meant a protein or polypeptide that has the basic biological functionality of the human ASP2 protein. Such basic biological functionality would be appreciated by a person skilled in the art to mean the ability to cleave APP as described herein. The term ASP2 protein includes the wild type form of the ASP2 enzyme, as well as modified forms of the ASP2 enzyme. Modification may be, for example by conventional molecular biological techniques such as the addition, substitution or deletion of one or more amino acids; or indeed fragments of the ASP2 enzyme, provided that such modified forms or fragments have the basic biological functionality of the wild type ASP2 protein. A person skilled in the art would easily be able to test whether such modified forms or fragments retained such basic biological functionality by assaying for cleavage of amyloid precursor protein which is known to be the substrate for the enzyme. Preferably, however, the ASP2 protein is the wild type protein, with the sequence given in SEQ ID 1, and in reference 42. Preferably, the nucleotide sequence encoding the human ASP2 protein is such that it encodes the protein with the sequence given in SEQ ID 1 and in reference 42.

The nucleotide sequence encoding the human ASP2 protein may be selected from the following group:

a) a polynucleotide comprising a polynucleotide sequence encoding a polypeptide sequence having at least 95%, 96%, 97%, 98%, or 99% identity to the polypeptide sequence of SEQ ID NO:1;

b) a polynucleotide comprising a polynucleotide sequence which encodes the polypeptide of SEQ ID NO:1;

c) a polynucleotide which encodes a polypeptide sequence having at least 95%, 96%, 97%, 98%, or 99% identity to the polypeptide sequence of SEQ ID NO:1;

d) a polynucleotide which encodes the polypeptide of SEQ ID NO:1;

e) a polynucleotide having or comprising a polynucleotide sequence encoding a polypeptide sequence that has an Identity Index of 0.95, 0.96, 0.97, 0.98, or 0.99 compared to the polypeptide sequence of SEQ ID NO:1;

The CamKII promoter is described in references 32 and 33

Transgenic animals of the invention may develop amyloid plaques and are therefore useful as a model of Alzhiemer's disease and other neurodegenerative disorders.

A "transgene" comprises a polynucleotide, isolated from nature, which has been manipulated in-vitro and which can be subsequently introduced into the genome of the same or a different species in either the native or modified forms, such that it is stably and heritably maintained in that genome. The polynucleotide preferably encodes a protein of interest, and is generally operatively linked to a regulatory sequence. The term transgene is herein used to refer to the polynucleotide and the regulatory sequences to which it is operably linked. The transgene may further comprise other polynucleotides which encode, for example, reporter genes in order to monitor expression of the transgene. An organism into which a transgene has been introduced is termed a "transgenic organism". A transgenic construct is a vector construct comprising the transgene.

The term "transgenic DNA" as used herein refers to the polynucleotide comprised within the transgene, which polynucleotide encodes the protein of interest. The present invention relies on the use of a nucleic acid construct to generate a transgenic animal model for screening agents for potential use in the treatment of neurological disorders, in particular Alzheimers disease. The construct comprises a nucleotide sequence encoding the human ASP2 protein, operatively linked to a mouse CaM-K-II promoter. In a preferred embodiment, the nucleic acid construct further comprises a Internal Ribosomal Entry Site (IRES) downstream (3') of the nucleotide encoding the human ASP2 protein, and a nucleic acid sequence encoding a reporter gene downstream of the IRES. This type of construct is termed bi-cistronic, and enables separate expression of both the human ASP 2 protein, and the reporter protein. The reporter protein may be, for example, luciferase, green fluorescent protein or derivatives thereof, or β galactosidase, but preferably it is β galactosidase. The advantage of such a construct is that it enables one to monitor human ASP2 expression by monitoring expression of the reporter gene.

The assembly of the transgenic construct follows standard cloning techniques, that are well known in the art (for example see ref 8). The ASP2-encoding polynucleotide may consist of cDNA or genomic DNA. If it is cDNA, the cDNA to be overexpressed can be prepared from a mRNA extracted from a relevant tissue, preferably a tissue in which the ASP2 protein is known to be expressed, or alternatively can be extracted by probing a human cDNA library.

The DNA, along with the CaMKII promoter and any other desired components such as artificial introns, the IRES, or a reporter gene can then be inserted into a cloning vector by restriction digest and ligation. Suitable cloning vectors for the assembly of transgenes are those which provide for acceptable yields of DNA. Any commercially available plasmid vector or phage that can carry a cDNA and which can be manipulated to contain a selection marker is suitable.

The CaM-K-II promoter is operably linked to the coding sequence of the ASP2 encoding polynucleotide in a manner that will permit the required temporal and spatial expression of the polynucleotide. There may or may not be intervening sequences between the linked polynucleotide and the promoter, provided that the promoter directs expression of the ASP2 encoding polynucleotide so linked to it. Methods of so linking regulatory sequences to cDNAs to facilitate their expression are widely known in the art. Such methods include, for example, directly ligating the nucleic acid comprising the CaMK-II promoter to the coding region of the ASP2 encoding polynucleotide. Additional nucleic acid sequences may be included that modulate expression in the required manner. Examples of additional sequences include enhancer elements, artificial intron and others.

In addition the nucleotide sequence of the CaMK-II promoter, or other regulatory sequence, may be modified to increase levels of expression. Such modifications can be achieved using, for example, site-directed mutagenesis methods well known in the art (see ref 8, supra).

In addition to modifying the sequence of regulatory elements to enhance, or otherwise change, expression levels, the coding sequence of the ASP2 encoding polynucleotide may be modified to enhance or otherwise affect expression levels. For example if the transgenic DNA is from a different species than the host, the codon usage of the transgenic DNA can be altered to match more closely that of the host. It is well known in the art that different organisms use the 64 coding and stop codons at different frequencies. Codons that are infrequently used in an organism are termed "rare codons". If the transgenic DNA includes a codon that is a rare codon in the host, expression levels may be severely reduced. One solution is to replace one or more rare codons in the transgenic DNA with codons that are frequently used in the host. Other modifications to the transgenic DNA sequence include modifying the polynucleotide sequence surrounding the start codon (the initiator methionine encoding codon) to make this more closely match the consensus "Kozak" sequence (A/G CCATGG, where the ATG in bold is the start codon; see for example ref 9. In the transcribed mRNA molecule the Kozak sequence is believed to provide the optimal environment for initiation of translation of the polypeptide.

Preferably, prior to the introduction of the transgene into the host cell, the vector portions are removed by restriction enzyme digestion, for example by using restriction sites in the vector that flank the transgene. Thus the genetic material that is actually introduced into the host cell will preferably comprise the coding sequence of the ASP2 encoding polynucleotide and the regulatory sequences to which it has been operably linked together with other potential components of the transgene, for example a reporter gene. An example of this technique is given in reference 10.

An inducible system such as described in Ref 11 may also be used, which has the advantage of regulating the gene expression (induction/repression). For example, the tetracycline-inducible system (Refs. 12, 13) uses two constructs: a minimal promoter (PhCMV*-1) fused to seven tetracyclic operator sequences and the cDNA in question; and a trangene containing the tetracycline-controlled tranactivator protein (tTA) coding sequence under the control of a promoter, for example taken from the following list: Human APP (ref. 14); rat neuron specific enolase (neurons) (ref. 15); human β actin (ref. 16); human PDGFβ (ref. 17); mouse Thy 1 (ref. 18); mouse Prion protein promoter (PrP) (ref. 19); Syrian hamster Prion protein promoter (ref. 20 and 21); rat synapsin 1 (brain) (ref. 22); human FMR1 (brain) (ref. 23); human neurofilament low (ref. 24), middle (brain) (ref. 25); NEX-1 (brain) (ref. 26); mouse APLP2 (brain) (ref. 27); rat alpha tubulin (ref. 28); mouse transferrin (ref. 29); mouse HMGCR (3-hydroxy-3-methylglutaryl coenzyme A reductase, oligodendrocytes) (ref. 30), mouse myelin basic protein (ref. 31), mouse CaM-kinase-II promoter (ref. 32 and 33), human thy-1 promoter (ref. 34), JC viral early region promoter (ref. 35), or human neurofilament NF-L transcriptional regulatory sequences (ref. 36). Each construct is used to generate a transgenic mouse. Crossing the two homozygous mice generates a double transgenic line which expresses the tTA according to the chosen promoter. This tTA induces expression of the cDNA by activating the PhCMV*-1, but only in the absence of tetracycline. In the presence of tetracycline there is only basal expression.

Generation of transgenic non-human mammals of the invention may be carried out conventionally, for example as described in WO93/14200, WO91/19810, WO93/02189, WO89/00689, WO92/06187, EP0451700, WO92/13069 and WO89/06689.

There are a number of techniques that permit the introduction of genetic material, such as a transgene, into the germline. The most commonly used, and preferred protocol comprises direct injection of the transgene into the male pronucleus of the fertilised egg (ref 10), resulting in the random integration into one locus of a varying number of copies, usually in a head to tail array (ref 37). The injected eggs are then re-transferred into the uteri of pseudo-pregnant recipient mothers. Some of the resulting offspring may have one or several copies of the transgene integrated into their genomes, usually in one integration site. These "founder" animals are then bred to establish transgenic lines and to back-cross into the genetic background of choice. It is convenient to have the transgene insertion on both chromosomes (homozygosity) as this obviates the need for repeated genotyping in the course of routine mouse husbandry.

Alternatively, for the production of transgenic mice, transgenes can be introduced via embryonic stem (ES) cells, using electroporation, retroviral vectors or lipofection for gene transfer. This is followed by the random insertion into the genome of the pluripotent embryonic stem (ES) cells, followed by the production of chimeric mice and subsequent germline transmission. Transgenes of up to several hundred kilobases of rodentian DNA have been used to produce transgenic mice in this manner (for example refs 38, 39). The latter approach can be tailored such that the transgene is inserted into a pre-determined locus (non-randomly, for example ROSA26 or HPRT) that supports ubiquitous as well as tissue specific expression of the transgene (ref 40).

In one aspect, the transgenic non-human mammal is generated by introduction of the transgenic construct into an embryo, insertion of the embryo into a surrogate mother and allowing the embryo to develop to term.

The construct is prepared for transfer to the host animal by cleavage of vector containing the construct and purification of the DNA (ref. 8)

The transfer is carried out conventionally preferably using microinjection as described in detail in reference 8.

In an alternative aspect the parent transgenic non-human mammal is produced by introduction of the construct into embryonic stem cells by conventional methods such as calcium phosphate/DNA precipitation, direct injection or electroporation (ref. 9) followed by injection of the transformed cells into blastocytes and insertion of the resulting embryo into a surrogate mother as described above.

Transgenic animals may be identified by testing to ensure the required genotypic change has been effected. This may be done in any suitable fashion, for example by detecting the presence of the transgene by PCR with specific primers, or by southern blotting, preferably of tail DNA, with a specific probe.

Once the desired genotype has been confirmed, the transgenic animal line can be subjected to various tests to determine the phenotype. The tests involved in this phenotypic characterisation depend on what genotypic change has been effected, and may include, for example, morphological, biochemical and behavioural studies. The transgenic animals of the present invention may demonstrate increased cleavage of APP at the $\beta$ site, leading to greater levels of A$\beta$ an C terminal fragments of APP. This would lead to increased $\chi$ cleavage and an increase in amyloid burden. Gross phenotypic effects expected may be a decrease in cognition which can be tested in conventional behavioural tests such as the Morris Water Maze and the Y Maze.

This invention also includes any cells cultured from the transgenic non-human animal. The cells are cultured in-vitro. The genome of the cells can thus comprise the construct of the invention. The human ASP2 polypeptide is typically expressed in such cells in an amount at least 2, preferably at least 3, 4 or 5 times greater than the amount of endogenous ASP2 polypeptide that is expressed in the cells.

Cells cultured in-vitro from a transgenic animal may be prepared by any suitable method. The cells are typically rodent and preferably mouse cells. Cultures of neuronal cells can therefore be provided, for example cultures of primary hippocampal cells. The cells may be used to introduce other genes of interest by any known method (including viral delivery).

The transgenic non-human mammal is preferably a rodent such as rat or mouse, more preferably a mouse.

The appropriate transgenic DNA sequence may be inserted into the vector by a variety of procedures. In general, the transgenic DNA sequence is inserted into an appropriate restriction endonuclease site(s) by procedures known in the art. Such procedures and others are deemed to be within the scope of those skilled in the art.

The use of non-human animal models which overexpress or lack more than one gene can provide important insights into the interaction of different genetic loci in particular diseases, for example Alzheimers Disease. Consequently the interbreeding of the ASP2 transgenic non-human animals of the present invention with non-human animal models which overexpress or underexpress a different gene may produce alternative and potentially superior animal models of diseases such as Alzheimers. For example, the ASP2 transgenic non-human animals of the present invention may be crossed with mice bearing a transgene comprising a nucleotide encoding the human mutant Amyloid Precursor Protein K670N, M671L (the "Swedish" mutation) (such mice are described in European Patent Application EP1063298). In another aspect, the ASP2 transgenic non-human animals of the present invention may be crossed with mice bearing a transgene comprising a nucleotide encoding the human mutant Amyloid Precursor Protein, V717I (the "London" mutation) (such mice are described in ref 41).

Suitable promoters for the second transgene include: Human APP (ref. 14); rat neuron specific enolase (neurons) (ref. 15); human $\beta$ actin (ref. 16); human PDGF$\beta$ (ref. 17); mouse Thy 1 (ref. 18); mouse Prion protein promoter (PrP) (ref. 19); Syrian hamster Prion protein promoter (ref. 20 and 21); rat synapsin 1 (brain) (ref. 22); human FMR1 (brain) (ref. 23); human neurofilament low (ref. 24), middle (brain) (ref. 25); NEX-1 (brain) (ref. 26); mouse APLP2 (brain) (ref. 27); rat alpha tubulin (ref. 28); mouse transferrin (ref. 29); mouse HMGCR (3-hydroxy-3-methylglutaryl coenzyme A reductase, oligodendrocytes) (ref. 30), mouse myelin basic protein (ref. 31), mouse CaM-kinase-II promoter (ref. 32 and 33), human thy-1 promoter (ref. 34), JC viral early region promoter (ref. 35), or human neurofilament NF-L transcriptional regulatory sequences (ref. 36).

However, it is preferable that both of the precursor transgenic non-human animal lines comprise transgenes which are operably linked to a neuronal specific promoter, for example the CamKII promoter. This ensures that in the non-human animal produced by the cross, both transgenic DNAs are expressed in a neuronal specific manner.

In a preferred embodiment, a non-human transgenic animal is generated by crossing the ASP2 lines of the present invention with a non-human transgenic animal whose cells contain a transgene comprising a nucleotide encoding the human Amyloid Precursor Protein. Particularly preferred is when said APP encoding nucleotide is operably linked to the CamKII promoter, or the the Thy 1 promoter. Said human APP may be wild type APP, or may contain mutations such as the Swedish or London mutation, or any other known mutations as described in ref 7.

Such transgenic non-human animals containing more than one transgene wherein one of the transgenes comprises a nucleotide encoding the human Asp2 protein operably linked to the CamKII promoter are also part of the invention, and may be used as described herein.

The transgenic non-human mammal or cells of the invention may be used to screen for therapeutic agents which inhibit the activity of ASP2, and consequently the processing of APP and amyloid deposits, by administering test therapeutic agent to the mammal or cell culture medium and observing changes in the activity of ASP2. Such changes may be measured by, for example, looking for a decrease in A$\beta$ production which may be measured biochemically, or looking for a decrease in plaque burden or a delay in deposition of plaques, which may be measured by physiochemical techniques. The action of therapeutic agents may also be measured by improvements in behavioural tests. Suitable tests are given in ref 41. The invention extends to such method of screening. Suitable techniques for making such observations are described in WO93/14200.

Potential therapeutic agents may inhibit (antagonise) the activity of the ASP2 protein. Preferably, said therapeutic agent is also screened against a non-human transgenic animal which overexpresses aspartyl protease 1, in order to confirm either that the therapeutic agent does not also inhibit asp 1, or that if it does inhibit asp1 there are no adverse effects from this inhibition. An example of the production of a transgenic non-human animal overexpressing asp1 is given in the examples of this specification.

A method of identifying a therapeutic agent for the treatment of a condition characterised by an increase in APP processing, an increase in amyloid deposits and a decrease in cognition can therefore be provided, comprising:

administering to an animal of the invention a candidate test substance and determining whether the candidate substance (i) prevents or delays the onset of the condition or (ii) treats the condition.

Option (ii) may be tested by determining whether the candidate substance causes a decrease in any of the cellular or physiological changes caused by the condition. Such cellular or physiological changes may include changes in APP processing, amyloid deposition, or cognition.

A method of identifying a therapeutic agent for the treatment of a condition characterised by an increase in APP processing, an increase in amyloid deposits and a decrease in cognition can also be provided, comprising:

contacting a candidate substance with a cell of the invention, and determining whether the candidate substance (i) prevents or delays the onset of cellular changes associated with the condition, or (ii) causes a decrease in any of the cellular changes caused by the condition (such as any of the cellular changes mentioned herein, in particular the level of APP processing).

In the method where the candidate substance is contacted with a cell of the invention, the method may be intended to identify protease inhibitors as antagonists of ASP2, or may be intended to identify neuroprotective agents. It is likely that cells of the invention overexpressing ASP2 may be sensitive to neurotoxic insults such as glutamate, kainate, serum and potassium withdrawal. Reversal or prevention of the effects of these agents in a cell of the invention by a candidate substance is an indication that said candidate substance may be a neuroprotective agent.

Suitable candidate substances which may be tested in the above methods include antibody products (for example, monoclonal and polyclonal antibodies, single chain antibodies, chimeric antibodies and CDR grafted antibodies). Furthermore, combinatorial libraries, defined chemical identities, small molecules, peptide and peptide mimetics, oligonucleotides and natural product libraries, such as display libraries (e.g. phage display libraries) may also be tested. The candidate substances may be chemical compounds. Batches of the candidate substances may be used in an initial screen of, for example, ten substances per reaction, and the substances of batches which show inhibition tested individually.

Agents which may reverse the phenotypic changes such as an increase in APP processing, an increase in amyloid deposits, and deficits in cognition seen in the transgenic animals of the invention may be tested in-vivo or in cells or tissue preparations in-vitro. Compounds can be tested using the assays and tests used to characterise the invention. For example, after administration of any potential therapeutic agent, the response of the transgenic animal may be assessed by, for example, looking for an improvement in cognition, or a decrease in APP processing or amyloid deposits as described in the Examples. Methods for screening potential therapeutic agents using cell lines or animals are established. ELISA or Homogenous Time Resolved Fuorescence (HTRF) methodologies can be used.

Agents identified in the screening methods of the invention may be used to prevent or treat the diseases discussed above, in particular Alzheimers Disease. The condition of a patient suffering from such a disease can therefore be improved by administration of such a product. The formulation of the product for use in preventing or treating the disease will depend upon factors such as the nature of the agent identified and the disease to be prevented or treated. Typically the agent is formulated for use with a pharmaceutically acceptable carrier or diluent. For example it may be formulated for intracranial, parenteral, intravenous, intramuscular, subcutaneous, transdermal or oral administration. A physician will be able to determine the required route of administration for each particular patient. The pharmaceutical carrier or diluent may be, for example, an isotonic solution.

The dose of product may be determined according to various parameters, especially according to the substance used; the age, weight and condition of the patient to be treated; the route of administration; and the required regimen. A suitable dose may however be from 0.1 to 100 mg/kg body weight such as 1 to 40 mg/kg body weight. Again, a physician will be able to determine the required route of administration and dosage for any particular patient.

The construct, cells or therapeutic agents of the invention may be present in a substantially isolated form. It will be understood that they may be mixed with carriers or diluents which will not interfere with their intended purpose and still be regarded as substantially isolated. Thus the construct, cell or therapeutic agent of the invention may also be in a substantially purified form, in which case it will generally comprise more than 90%, e.g. more 95%, 98% or 99%, by weight of the relevant preparation.

EXAMPLES

Generation of Transgenic Mice Expressing ASP2

The ASP2 cDNA, with the sequence referred to in ref 42, was prepared in accordance with conventional techniques. To generate the Asp2 mis-expression transgenes, the Asp2 cDNA is cloned into the vector pCamKIRESbgal.

This vector contains the mouse calcium-calmodulin-dependent kinase II$\alpha$ (CamKII $\alpha$) promoter, which has previously been shown to direct transgene expression to both the hippocampus and neocortex of the mouse forebrain (Ref 32)). The promoter was isolated in the manner described in ref 32 (see reference note 20). Then, an 8.5 kb SalI promoter fragment was isolated by restriction digestion. This was ligated into Arm3 vector (a derivative of pBluescript with the sites indicated flanking the SacI-KpnI pBluescript polylinker) digested with XhoI and SalI. This generated Arm3-CamKII (the 5' SalI site is destroyed). The 5Isolate form AS210S (a derivative of Plasmid AS210 (obtained from Stem Cell Sciences, Melbourne) contains the IRES-bgal-intron-polyA fragment as an XbaI-XhoI restriction fragment. The XbaI site was converted to a SalI site (to create AS210S), and the resultant SalI/XhoI fragment containing the IRES-bgal-intron-polyA cassette was ligated into the SalI site of Arm3-CamKII to generate CamKII-IRES-bgal. This contains unique NotI and SalI sites for the insertion of cDNAs. In the resulting vector, the promoter is upstream of a cassette containing the picornaviral internal ribosome-entry site (IRES) (Ref 35) and the gene for beta-galactosidase and SV40 transcription termination signals. The Asp2 cDNA was then inserted between the CamKII promoter and the IRES using the NotI and SalI sites. Transcription which initiates at the CamKIIα promoter capsite and terminates at the SV40 polyadenylation signals therefore results in a dicistronic message encoding APPV46F and beta-galactosidase proteins. The latter can be easily detected to confirm that transgene expression has taken place. The inclusion of a beta-galactosidase reporter gene in the construct enables simple, accurate and sensitive detection of cellular sites of transgene expression. This cloning process is shown schematically in FIG. 1.

The above described construct was used to generate transgenic mice by the following procedures:

The construct was prepared and purified.

Female mice were induced to superovulate and embryos are recovered.

DNA was microinjected into the pronucleus of embryos.

Embryos were transferred into pseudopregnant mice (female mice previously paired with vasectomised males).

Embryos were allowed to develop normally and mice are born.

Founder mice were identified by Southern blot and PCR and bred on.

Suitable mice lines are as follows;

Donor mice (embryos for pronucleus injection): [C57B1/6×CBA]F2 hybrid

Acceptor mice: [C57B1/6×CBA]F1 hybrid

Mice for further breeding: C57B1/6

Confirmation that the Transgenic Mice do Express Asp 2 in a Neuronal Specific Manner The construct used to express the Asp2 cDNA was designed to enable monitoring of tissue specificity of expression by staining sections from the transgenic animals for β-galactosidase. In order to compare expression of the transgene with expression of endogenous Asp2, a knock out mouse was generated with the LacZ reporter gene used in a vector comprising the endogenous Asp2 promoter. This provided a simple way of checking expression from the endogenous Asp2 promoter, again by staining for β-galactosidase.

Whole brains were harvested from Asp2 overexpressor line and the comparative knock out line and processed for β-galactosidase staining.

Parasaggital sections were cut in order to show clearly the distribution of staining within the brain. The results are shown in FIG. 2. No staining for LacZ was seen in Wild Type brains (FIG. 2c). The knock out mouse brain sections clearly show LacZ expression localised to the Hippocampus, cortex and reduced LacZ expression in the Caudate Striatum, Medulla and Forebrain (FIGS. 2a,b). In the Asp2 overexpressor mouse brains (FIGS. 2d, e), LacZ expression is clearly localised to the hippocampus and caudate striatum in line 17 with heavier staining extending to the Cortex in line 4. The expression pattern of the transgene shown in lines 17 and 4 under control of the camKII promoter clearly replicates that seen in the knock out mouse where the enodgenous promoter directs LacZ expression. In Alzheimers Disease patients plaques and tangles are most often seen in the cortex and in the hippocampous. Thus overexpression of Asp2 protein is appropriately located to faithfully reproduce the endogenous neuronal expression of Asp2.

Generation of Transgenic Mice Overexpressing Asp1

The asp1 DNA, with the sequence referred to in reference 43 was prepared by conventional methods. This was then cloned into the vector pCamKIRESβGal as described above.

The asp1 transgenic construct was used to generate transgenic mice by the following procedures:

The construct was prepared and purified.

Female mice were induced to superovulate and embryos are recovered.

DNA was microinjected into the pronucleus of embryos.

Embryos were transferred into pseudopregnant mice (female mice previously paired with vasectomised males).

Embryos were allowed to develop normally and mice are born.

Founder mice were identified by Southern blot and PCR and bred on.

Suitable mice lines are as follows;

Donor mice (embryos for pronucleus injection): [C57B1/6×CBA]F2 hybrid

Acceptor mice: [C57B1/6×CBA]F1 hybrid

Mice for further breeding: C57B1/6

Crossbreeding of Transgenic Mice to Generate Carriers of Two Transgenes

The transgenic mice expressing Asp2 and the further desired transgene, for example amyloid precursor protein which may be wild type APP, or APP bearing a familial mutation such as the Swedish or London mutation, are crossbred and the offspring genotyped to select those with both of the transgenes. Preferably, both transgenes are under the control of the CamKII promoter. If the Asp2 transgene is 'a' and the second transgene is 'b', then the following mating pattern is possible from heterozygous parents with two independently segregating genes:

| Alleles | b | — |
|---|---|---|
| a | a b | a — |
| — | — b | — — |

One in four offspring would be a double overexpressor, two in four would be single overexpressors (one for each transgene) and one in four offspring would be a wild type mouse. This cross can be used to calculate the number of parents required to produce an experimental cohort of double overexpressors.

Screening of Drugs Using Transgenic Mice

The transgenic mice described above may be used to screen for potential activity of test drugs in the treatment of Alzheimer's disease and other neurodegenerative disorders.

APP expression and processing may be examined using detection of mRNA by Northern blots and detection of polypeptides using polyclonal and monoclonal antibodies that are specific to the terminal regions of the target peptides.

Histopathological observations may be made using immunohistological techniques to permit identification of amyloid plaques and related deposits such as hyperphosphorylated tau and in situ hybridisation using labelled probes to target mRNA.

Analyses of Mouse Brain

Animals are culled by overdose of anaesthetic. Brains are removed and hemisected down the midline. The halves are placed in either 10% formal saline or snap frozen.

Extraction of Aβ and APP from Mouse Brain for Immunoassay

Snap frozen half brains are weighed and then homogenised using a Polytron homogeniser on maximum speed for 30 seconds. Homogenates are prepared at 20% wt/vol in 50 mM Tris-HCl, 150 mM NaCl, pH 8 with complete TM protease inhibitor (Boehringer Mannheim) added on the day according to the manufacturer's instructions. Homogenates are then diluted with an equal volume of 50 mM Tris-HCl, 150 mM NaCl pH 8 containing 1% Nonidet P40 (10% solution, Pierce), 1% deoxycholate, 0.4% sodium dodecyl sulphate and complete TM (as above). Homogenates are then sonicated in a water bath sonicator for 45 minutes and then boiled for 10 minutes in a large beaker of water. The homogenates are then transferred to 1.5 ml Eppendorf tubes and centrifuged at 12000 rpm for 10 minutes. The supernatants are removed and stored in aliquots at −20° C.

Immunocytochemical Assessment of Brains from Transgenic Mice

Hemisected mouse brain, stored in formal saline, is embedded in paraffin wax and cut into 10 μm sections on a microtome before mounting onto gelatin subbed slides. For immunocytochemistry, sections are dewaxed and rehydrated by standard techniques. Sections being assessed for Aβ or APP content are treated with 80% formic acid after rehydration. For other sections, boiling for 10 minutes in 0.1M citrate buffer in a microwave oven enhances immunoreactivity. Endogenous peroxidase is blocked by incubating with hydrogen peroxide (0.3% in phosphate buffered saline for 30 minutes). Primary antibodies for Aβ (1E8—monoclonal to Aβ 13–27; G210—monoclonal to ABeta 33–40; 20G10 and 5G5—monoclonals to Aβ 35–42, APP (22C11—Weidemann et al, 1989), glial fibrillary acidic protein (anti-GFAP, Boehringer Mannheim), neuronal markers (synaptophysin, MAP-2, choline acetyl transferase—Boehringer Mannheim) and normal and hyperphosphorylated tau (Innogenetics) are incubated with the sections overnight at 4° C. Sections are visualised using DAB (Vector Labs) and after dehydration are mounted in DPX aqueous mountant.

Protein Assay

Mouse brain homogenates are assayed for protein before gel electrophoresis to ensure equal protein loading between samples for comparison of expression levels. The proteins are measured by the Bradford dye-binding procedure (Ref 28) using Bio-Rad (Herts, UK) dye reagent concentrate. The assay is carried out in a 96 well plate with the absorbance read at 595 nm using a Spectramax plate reader with software to analyse the results. As various reagents, particularly detergents, interfere with the Bradford assay calibrations are carried out in the appropriate sample vehicle.

SDS-PAGE

Proteins are fractionated using a Novex mini-gel system (R & D Systems Europe Ltd, Oxon, UK). An equal amount of protein is loaded for comparison of APP expression levels between animals. Samples are diluted in 2× reducing sample buffer containing 0.1M Tris pH6.8, 10% sodium dodecyl sulphate (SDS), 0.1% bromophenol blue in glycerol and 50% β-mercaptoethanol. The proteins are separated on a 6% Tris-glycine polyacrylamide gel containing SDS (Ref. 29) for 90 minutes at 125 volts. Protein standards are included of known molecular weight (Sigma) as well as a secreted APP standard (Pichia expressed, see Ref 32).

Western Blot Analysis

After SDS-PAGE the gels are washed for 5 minutes in transfer buffer containing 2.5 mM Tris, 19.2 mM glycine, 20% methanol at pH 8.3. The proteins are transferred from the gel onto 0.45 um nitrocellulose membrane (Schleicher & Schuell) using a Bio-rad semi-dry system for 2 hours at 0.8 mA/cm$^2$. After transfer the proteins are visualised on the membrane by staining with a 10% solution of Ponceau S (Sigma) for 2 minutes. This is destained by rinsing with distilled water.

The membrane is blocked in phosphate buffered saline (PBS) containing 10% dried milk powder for at least 1 hour at room temperature. WO2, monoclonal antibody raised against human Aβ 1–16, is incubated at 1 ug/ml in PBS overnight at 4° C. This is followed by three 10 minute washes in PBS. Secondary antibody is then added, this was anti-mouse horseradish peroxidase (Amersham NA931) at ¹⁄₃₀₀₀ dilution in PBS containing 4% bovine serum albumin and 0.1% Tween 20 incubated for 1 hour at room temperature. PBS washes are repeated as above and then the membrane transferred to a clean dish for addition of enhanced chemiluminescence substrate (Amersham RPN2106). The immunoreactive bands are detected using Hyperfilm-ECL (Amersham) which was developed using an automated processor (X-OGraph Compact X4). APP bands are scanned using a Fluor-S MultiImager (Bio-rad) linked to a computer with software for processing data.

Determination of the Concentration of Aβ 1–40 and 1–42 by Immunoassay

For the immunoassay of Aβ 1–40, plates (Gibco BRL, flat bottom 96 well plate, catalogue #1-67008-A) are coated (overnight at 4° C.) with 2F12 capture antibody, raised to Aβ 1–16 peptide, at 0.8 μg/ml in PBS. After coating, antibody solution is aspirated and plates blocked by incubating for 60 minutes at 37° C. with 1% gelatine v/v (Amersham RPN416) in assay buffer (50 mM Tris HCl, 150 mM NaCl, 0.5% bovine gamma globulins, 0.05% Tween 20, pH 7.4, passed through a 0.2 um filter before use). Following blocking, plates are washed 4×250 ul with phosphate buffered saline with Tween 20 (Sigma Cat No P3563). Samples of mouse brain extract prepared as described above are added to the plates together with the detection antibody, biotinylated G210 (1 μg/ml in assay buffer) raised to an Aβ 40 C-terminal peptide (Ref 30). The 2F12 coated plate containing brain extract and 150 ul of detection antibody is incubated overnight at 4° C. Plates are subsequently washed (4×250 ul) with phosphate buffered saline with Tween 20.

Quantitation of peptide-antibody complexation is achieved by the binding of strepatavidin-Europium. To each well is added 200 ul streptavidin-Europium (Wallac, Catalogue #1244-360) diluted 1:500 in 0.5% BSA, 0.05% γ-Globulin, 0.01% Tween 20, 20 uM DTPA (Sigma D 6518) in Tris buffered saline pH 7.4. Plates are incubated at room temperature for 60 minutes before washing with phosphate buffered saline. Finally, 200 ul of enhancer solution (Wallac, Catalogue #1244-105) is added to each well and the plate shaken for 5 minutes at room temperature before measurement of emission by time-resolved fluorescence on a Wallac 1234 Delfia Fluorometer.

For the determination of Aβ 1–42, plates are coated with the monoclonal antibody 5G5 (1 μg/ml in phosphate buffered saline) raised to the Aβ 35–42 peptide. Detection is with biotin-6E10 antibody (Senetek PLC). All other details are exactly as for Aβ 1–40 determination.

Aβ 1–40 and 1–42 (California Peptide Research Inc) are used for the construction of standard curves. Peptides are dissolved in dimethyl sulphoxide and diluted in appropriate brain extract buffer. Standards of Aβ 1–40 and 1–42 are assayed with each batch of mouse brain extract. The concentration of Aβ 1–40 and 1–42 is calculated by reference to the immunoassay signal produced by known concentrations of peptide.

Determination of the Concentration of Full Length and Alpha-Secretase Cleaved APP by Immunoassay For the immunoassay of full length plus alpha-secretase cleaved APP (FL+sAPPα), plates (Gibco BRL, flat bottom 96 well plate, catalogue #1-67008-A) are coated (overnight at 4° C.) with WO2 capture antibody (Ref 37), raised to Aβ 1–16 peptide, at 2.7 µg/ml in PBS. After coating, antibody solution is aspirated and plates blocked by incubating for 60 minutes at 37° C. with 1% gelatine v/v (Amersham RPN416) in assay buffer (50 mM Tris HCl, 150 mM NaCl, 0.5% bovine gamma globulins, 0.05% Tween 20, pH 7.4, passed through a 0.2 um filter before use). Following blocking, plates are washed 4×250 ul with phosphate buffered saline with Tween 20 (Sigma Cat No P3563). Samples of mouse brain extract prepared as described above are added to the plates together with the detection antibody, a polyclonal raised to APP (Ref 31). The 2F 12 coated plate containing brain extract and 150 ul of detection antibody is incubated overnight at 4° C. Plates are subsequently washed (4×250 ul) with phosphate buffered saline with Tween 20.

Quantitation of peptide-antibody complexation is achieved by the binding of Europium-antirabbit IgG (Wallac) diluted 1:500 in 0.5% BSA, 0.05% □ Globulin, 0.01% Tween 20, 20 uM DTPA (Sigma D 6518) in Tris buffered saline pH 7.4. Plates are incubated at room temperature for 60 minutes before washing with phosphate buffered saline. Finally, 200 ul of enhancer solution (Wallac, Catalogue #1244-105) is added to each well and the plate shaken for 5 minutes at room temperature before measurement of emission by time-resolved fluorescence on a Wallac 1234 Delfia Fluorometer.

Alpha-secretase cleaved secreted APP prepared from Pichia pasioris (see Ref 32) is used for the construction of a standard curve. The concentration of FL+sAPPα (this antibody format does not distinguish between full length and alpha-cleaved APP) is calculated by reference to the immunoassay signal produced by known concentrations of peptide.

Observation of Behavioural Changes

Observation of behavioural changes may employ conventional tests used to assess learning and memory deficits (Ref 44).

References

1. Dyrks T., Weidemann A., Multhaup G., Salbaum J. M., Lemaire H.-G., Kang J., Müller-Hill B., Masters C. L., Beyreuther K., EMBO J. 7, 949–957, (1988).
2. Hussain et al Molecular Cellular Neurosciences 16 pp 609–610 (2000)
3. Yan et al J. Biol Chem (papers in press in June 22) manuscript No M105583200
4. Dyrks T., Dyrks E., Mönning U., Urmoneit B., Turner J., Beyreuther K. FEBS Letters 335, 89–93, (1993).
5. Haass C., Hung A. Y., Schlossmacher M. G., Teplow D. B., Selkoe D. J. J. Biol. Chem., 268, 3021–3024, (1993).
6. Suzuki N.; Cheung T. T.; Cai X. D.; Odaka A.; Otvos L. Jr.; Eckman C.; Golde T. E., Younkin S. G. Science 264, 1336–1340, (1994).
7. Janus et al., 2000 Biochenimica et Biophysica Acta 1502 63–75
8. Sambrook et al, Molecular Cloning: A laboratory Manual, $2^{nd}$ Ed. Cold Spring Harbor
9. Kozak, M., Nucleic Acids Res (1984) May 11;12(9) :3873–3893
10. Hogan et al., 'Manipulating the mouse embryo', Cold Spring Harbor Laboratory, Cold Spring Harbor (1994).
11. Rossi and Blau, Current Opinion in Biotechnology, 9, 451–456 (1998).
12. Baron et al., Nucl. Acids Res. 23(17) 3605–6 (1995).
13. Furth et al., Proc. Natl. Acad., Sci., USA 91, 9302–9306 (1994).
14. Wirak D. O., et al Science 253, 323–325, (1991).
15. Forss-Petter et al., Neuron 5;197, (1990).
16. Ray et al., Genes and Development 5;2265–2273 (1991).
17. Sasahara et al., Cell 64;217–227 (1991).
18. Ingraham et al., Mol. Cell. Biol. 6(8) 2923–31 (1986).
19. M. Fischer et al., EMBO J. 15(6) 1255–64, (1996).
20. Scott et al., Prot. Sci. 1, 986–997 (1992).
21. Scott et al, Cell 59, 847–857 (1989)
22. Howland et al., Neurobiol. Aging 16(4) 685–99, (1995).
23. Hergersberg et al., Hum. Mol. Genet. 4(3) 359–66 (1995).
24. Thomas et al., J. Virol. 68(11) 7099–107 (1994).
25. Tu et al., J. Cell. Biol. 129(6) 1629–40 (1995).
26. Bartholoma et al., Mech. Dev. 48(3), 217–8 (1994).
27. Kock et al., J. Biol. Chem. 270(43) 25475–80 (1995).
28. Gloster et al., J. Neurosci. 14(12), 7319–30 (1994).
29. Thiesen et al., Mol. Cell. Biol. 13(12) 7666–76 (1993).
30. Duhamel-Clerin et al., Glia 11(1) 35–46 (1994).
31. Readhead et al., Cell 48;703–712 (1987).
32. Mayford et al. Science 274(5293) 1678–1693 (1996)
33. Tang, Y-P et al., Nature 1999, 401, 63–69
34. Kawabata S. Nature 354 476–478, (1991).
35. Sandhu F. A. J. Biol. Chem., 266 21331–21334, (1991).
36. Nalbantoglu et al., Nature 387: 500–505, (1997).
37. Costantini and Lacy, Nature 294, 92, 1981
38. Choi et al., Nature Genet. 4, 117–123 (1993)
39. Strauss et al., Science 259, 1904–07 (1993)
40. Vivian et al., BioTechniques 27, 154–162 (1999)
41. Moechars et al J. Biological Chemistry 274 pp 6834–6492.
42. Hussein et al Molecular and Cellular Neuroscience (1999) 14 pp 419–427
43. Acquati et al FEBS letters 468 (1) pp 59–64
44. Rogers DC et al, Mamm Genome. (1997) Oct;8(10) :711–3.

SEQ ID No.1
MAQALPWLLLWMGAGVLPAHGTQHGIRL-
PLRSGLGGAPLGLRLPRETDEEPEEP GRRGSFVEM-
VDNLRGKSGQGYYVEMTVGSPPQTLNIL-
VDTGSSNFAVGAAPHPF
LMRYYQRQLSSTYRDLRKGVYVPYTQGK-
WEGELGTDLVSIPHGPNVTVRAVIA AITESDKFFING-
SNWEGILGLAYAEIARPDDSLEPFFD-
SLVKQTHVPNLFSLQLCG
AGFPLNQSEVLASVGGSMIIGGIDH-
SLYTGSLWYTPIRREWYYEVIIVRVEINGQD LKMD-
CKEYNYDKSIVDSGTTNLRLP-
KKVFEAAVKSIKAASSTEKFPDGFWLGEQ
LVCWQAGTTPWNIFPVISLYLMGEVT-
NQSFRITILPQQYLRPVEDVATSQDDCYK FAISQSST-
GTVMGAVIMEGFYVVFDRARKRIG-
FAVSACHVHDEFRTAAVEGPFV
TLDMEDCGYNIPQTDESTLMTIAYVMAA-
ICALFMLPLCLMVCQWRCLRCLRQQ HDDFADDIS-
LLK

What is claimed is:

1. A recombinant DNA construct comprising a coding sequence encoding human aspartyl protease 2 (ASP2) and a brain-specific calcium calmodulin kinase II promoter sequence which is operably linked to the coding sequence.

2. A transgenic mouse whose genome incorporates a polynucleotide comprising a coding sequence which encodes the human ASP2 protein wherein said coding sequence is operably linked to a brain-specific calcium calmodulin kinase II promoter, and where said human Asp2 protein is expressed in the hippocampus of the mouse.

3. A transgenic mouse cell whose genome incorporates a nucleotide comprising a coding sequence which encodes the human ASP2 protein and a brain-specific calcium calmodulin kinase II promoter sequence which is operably linked to the coding sequence.

* * * * *

UNITED STATES PATENT AND TRADEMARK OFFICE
CERTIFICATE OF CORRECTION

PATENT NO. : 6,958,433 B2
DATED : October 25, 2005
INVENTOR(S) : Martin Geppert et al.

It is certified that error appears in the above-identified patent and that said Letters Patent is hereby corrected as shown below:

Title page,
Item [30], Foreign Application Priority Data, "0126732" should be -- 0126723 --.

Signed and Sealed this

Thirteenth Day of December, 2005

JON W. DUDAS
*Director of the United States Patent and Trademark Office*